United States Patent
Fujiwara et al.

Patent Number: 4,652,638
Date of Patent: Mar. 24, 1987

[54] 3-O-ACYL-4''-DEOXYDESMYCOSIN DERIVATIVES

[75] Inventors: Tatsuro Fujiwara; Kazuyo Ohta; Takao Hirano, all of Shizuoka, Japan

[73] Assignee: Toyo Jozo Kabushiki Kaisha, Shizuoka, Japan

[21] Appl. No.: 782,591

[22] Filed: Sep. 30, 1985

Related U.S. Application Data

[63] Continuation of Ser. No. 576,902, Feb. 3, 1984, abandoned.

[30] Foreign Application Priority Data

Feb. 3, 1983 [JP] Japan ................... 58-16624

[51] Int. Cl.$^4$ ........................... C07H 17/08
[52] U.S. Cl. ................................. 536/7.1
[58] Field of Search .......................... 536/7.1

[56] References Cited

U.S. PATENT DOCUMENTS 4,415,730 11/1983 Fujiwara et al. ............ 536/7.1
4,421,911 12/1983 Fujiwara et al. ............ 536/7.1
4,459,290 7/1984 Kirst et al. ................. 536/7.1

OTHER PUBLICATIONS

Migrdichian, *Organic Chemistry*, vol. 1, 1957, p. 311.

Primary Examiner—Johnnie R. Brown
Assistant Examiner—Elli Peselev
Attorney, Agent, or Firm—Young & Thompson

[57] ABSTRACT

Novel 3-O-acyl-4''-deoxydesmycosin derivatives of the formula

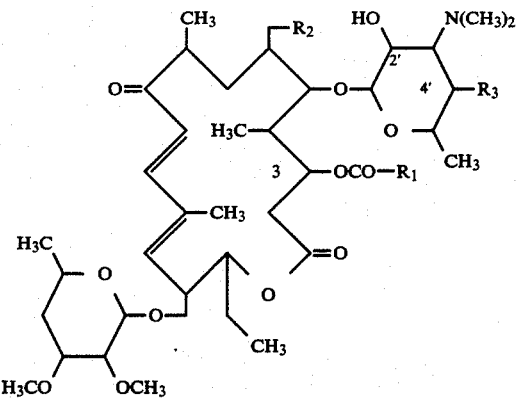

wherein $R_1$ is lower alkyl, phenyl, substituted phenyl, phenyl-lower alkyl or substituted phenyl-lower alkyl, $R_2$ is hydrogen or —CHO and $R_3$ is hydrogen or hydroxyl, or a non-toxic salt thereof, can be produced by acylating the hydroxyl group at position-3 of the corresponding intermediate while protecting the hydroxyl at position-2' or positions-2' and -4' with acetyl, and then removing the protective group or groups. These derivatives have antibiotic utility against Gram positive and Gram negative bacteria.

3 Claims, No Drawings

3-O-ACYL-4"-DEOXYDESMYCOSIN DERIVATIVES

This application is a continuation of application Ser. No. 576,902, filed Feb. 3, 1984, now abandoned.

This invention relates to novel 3-O-acyl-4"-deoxydesmycosin derivatives. More particularly, the present invention pertains to a compound of the formula

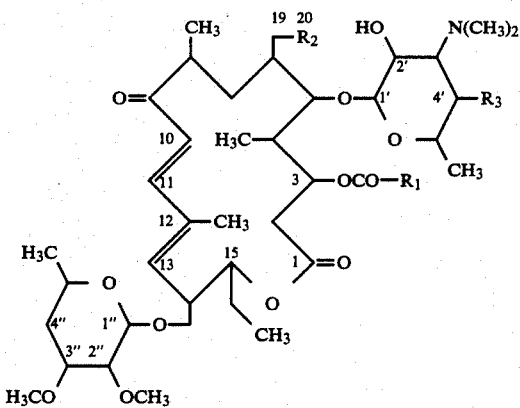

wherein $R_1$ is lower alkyl, phenyl, substituted phenyl, phenyl-lower alkyl or substituted phenyl-lower alkyl, $R_2$ is hydrogen or —CHO and $R_3$ is hydrogen or hydroxyl, or a non-toxic salt thereof.

Examples of pharmaceutically acceptable salts are salts of inorganic acids such as hydrochlorides, sulfates or phosphates and salts of organic acids such as acetates, propionates, tartrates, citrates, succinates, malates, aspartates or glutamates. Other non-toxic salts can be used.

The novel compound [1] has a stronger antibacterial activity against Gram positive bacteria than known macrolide antibiotics such as erythromycin and tylosin, and also has an equivalent level of antibacterial activity against Gram negative bacteria as compared with that of erythromycin, and hence may be useful for clinical use. The antibiotic also is useful for feed additives and growth stimulants.

The starting material [3] of the present invention is an intermediate, in which the hydroxyl group at positions-2' and -4', or the hydroxyl group at position-2' does not participate in the reaction, for production of a compound of the formula

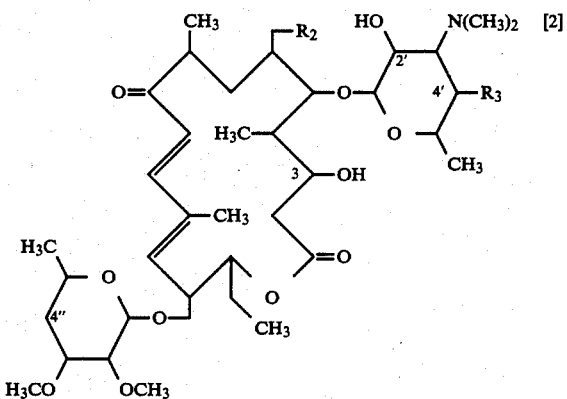

wherein $R_2$ and $R_3$ have the same meanings as hereinbefore, which is 4"-deoxydesmycosin when $R_2$ is —CHO and $R_3$ is hydroxyl (Jap. Pat. Unexam. Publ. No. 57-154197); 19-deformyl-4"-deoxydesmycosin when $R_2$ is hydrogen and $R_3$ is hydroxyl (Jap. Pat. Unexam. Publ. No. 58-13596), or 19-deformyl-4',4"-di-deoxydesmycosin, a 4',4"-di-deoxydesmycosin deformylated by $[(C_6H_5)_3P]_3RhCl$ in the presence of an inert organic solvent under heating, when $R_2$ and $R_3$ are hydrogen [Jap. Pat. Appln. No. 56-211648 (Jap. Pat. UNexam. Publ. No. 58-121299)].

Examples of protective groups are lower alkanoyls such as acetyl, propionyl or butyryl or halogenated acetyls such as chloroacetyl, dichloroacetyl, trichloroacetyl or trifluoroacetyl. Acetyl is preferred.

Starting material [3], for example, wherein the hydroxyl group at positions-2' and -4', or at position-2' is protected by acetyl can be produced as follows:

(1) 2',4'-di-O-acetyl-4'-deoxydesmycosin (an intermediate for 4"-deoxydesmycosin hereinbefore), wherein $R_2$ is —CHO and $R_3$ is hydroxyl, is produced by 2',4'-di-O-acetylating deoxymycosin, then 4"-O-trifluoromethane-sulfonylating, 4"-iodating and de-4"-iodating it (Jap. Pat. Unexam. Publ. No. 154197).

(2) 2'-O-acetyl-4',4"-di-deoxydesmycosin (an intermediate for 4',4"-di-deoxydesmycosin), wherein $R_2$ is —CHO and $R_3$ is hydroxyl, is produced by a process in which tylosin is 2'-O-acetylated, 4'-demycarosylated, 4"-O-acetylated, 4'-O-trifluoromethanesulfonylated, 4'-iodated, de-4'-O-acetylated, 4"-O-trifluoromethanesulfonylated, 4"-iodated and de-4',4"-diiodated (Jap. Pat. Unexam. Publ. No. 57-154197).

(3) 2',4'-di-O-acetyl-19-deformyl-4"-deoxydesmycosin (an intermediate for 19-deformyl-4"-deoxydesmycosin), wherein $R_2$ is hydroxyl and $R_3$ is hydroxyl, is produced by 2',4'-di-O-acetylating, 4"-O-trifluoromethanesulfonylating, 4"-iodating and de-4"-iodating 19-deformyl-desmycosin (Jap. Pat. Unexam. Publ. No. 56-55399), which in turn is obtained by deformylating desmycosin with $[(C_6H_5)_3P]_3RhCl$ in an inert organic solvent under heating (Jap. Pat. Unexam. Publ. No. 58-13596).

(4) 2'-O-acetyl-19-deformyl-4',4"-di-deoxydesmycosin (an intermediate for 19-deformyl-4',4"-di-deoxydesmycosin), wherein $R_2$ is hydrogen and $R_3$ is hydrogen, is produced by deformylating 2'-O-acetyl-4',4"-di-deoxydesmycosin with $[(C_6H_5)_3P]_3RhCl$ (Jap. Pat. Unexam. Publ. No. 57-154197) in an inert organic solvent under heating [Jap. Pat. Appln. No. 56-211648 (Jap. Pat. Unexam. Publ. No. 58-121299)].

Examples of inert organic solvents hereinabove are preferably benzene series solvents such as benzol. The deformylation reaction proceeds with reflux of the inert organic solvent. The reaction progress can be checked by silica-gel TLC or HPLC, and upon observing the disappearance of 2'-O-acetyl-4',4"-di-deoxydesmycosin, the reaction can be stopped. Extraction of the product from the reaction mixture can be performed by pouring the reaction mixture into water, adjusting to pH 8–9.5 by adding aqueous ammonia and extracting with a water-immiscible organic solvent such as chloroform.

In the present invention, hydroxyl at position-3 of compound [3] hereinbefore is acylated (hereinafter sometimes simply designated as 3-acylation), and the above carboxylic acid [4] is used as is or as a reactive derivative for an acylating agent.

Examples of carboxylic acid [4] are lower fatty acids such as acetic acid, propionic acid, butyric acid, isobutyric acid, valeric acid, isovaleric acid or optionally substituted benzoic acid, and optionally substituted phenyl-lower fatty acids such as phenylacetic acid, 2-phenylpropionic acid, 3-phenylpropionic acid, 2-phenylbutyric acid or 2-phenylisovaleric acid. The benzene ring of the above benzoic acid and phenyl-lower fatty acid may optionally be substituted by, for example, 1-3 lower alkyl, lower alkoxy, halogen or nitro.

The reactive derivatives hereinabove are acylating reagents usually used for acylation of hydroxyl groups in organic chemistry. For example, acid halides such as acid bromides and acid chlorides, acid anhydrides, mixed anhydrides, activated esters or acid azides can be used. Condensating reagents, for example known diimides such as N,N'-cyclohexylcarbodiimide (DCC), N-cyclohexyl-N'-2-(morpholyl-4)-ethylcarbodiimide or N-ethyl-N'-dimethylaminopropyl-carbodiimide, N,N'-carbonyl-bisimidazole or isoxazolium slats are also used for 3-acylating in direct acylation by carboxylic acid.

The above 3-acylation proceeds in an inert organic solvent Examples of preferred organic solvents are acetone, tetrahydrofuran, dioxane, dimethylformamide, dimethylacetamide, chloroform, dichloromethane and pyridine. In the acylation, if an acid is formed, a tertiary organic amine such as triethylamine, pyridine, picoline, collidine, quinoline, isoquinoline, N-methylpiperadine, N-methylmorpholine, dimethylaniline, dimethylaminopyridine or tribenzylamine is preferably added. The acylation reaction proceeds at room temperature but can be heated to =°-60° C. The reaction progress can be traced by TLC or HPLC and the reaction can be stopped upon observing the disappearance of the starting material [3].

Isolation of the reaction product of the formula

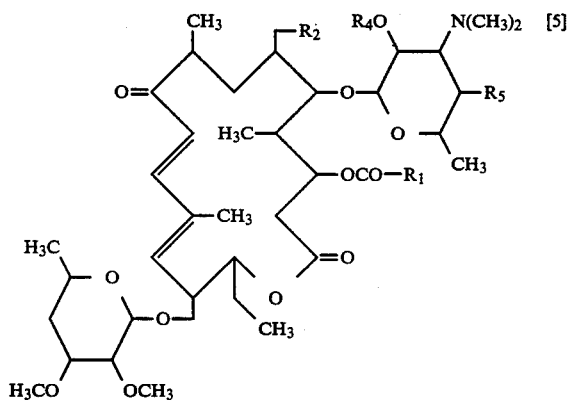

wherein $R_2$, $R_4$ and $R_5$ have the same meanings as hereinbefore, can be performed by adding water to the reaction mixture and extracting with a water-immiscible organic solvent such as chloroform, dichloroethane, methyl isobutyl ketone, ethyl acetate or butyl acetate at pH 8-9.5.

Further purification, if required, can be performed by the same procedure as for the starting material [3] hereinbefore.

Removal of the protective group for hydroxyl at positions-2' and 4', or hydroxyl at position-2' of the reaction product [5], especially an acetyl group, can be performed by heating in an optionally water-containing lower alcohol. Examples of lower alcohols are methanol or ethanol, preferably methanol. The progress of the above reaction can be traced by TLC and HPLC, and the reaction can be stopped upon observing the disappearance of compound [5].

Isolation of compound [1] from the reaction mixture can be performed by distilling off the lower alcohol, and extracting with a water-immiscible organic solvent such as chloroform, dichloromethane, dichloroethane, methyl isobutyl ketone, ethyl acetate or butyl acetate at pH 8-9.5. Further purification can be performed by column chromatography using silica-gel, activated alumina or an adsorption resin.

The minimum inhibitory concentrations (MIC) of the compounds of the present invention are shown in Tables 1 and 2. In each table, * shows the clinical isolates of erythromycin, oleandomycin and 16-membered macrolide antibiotic-resistant strains (macrolide-resistant bacteria A group).

The following examples illustrate the present invention. The Rf values in the examples are, if not specified, measured by the TLC of the following carrier and developers.

Carrier: Merck, DC-Fertigplatten Kiesel gel 60F$_{254}$, Art 5715.

Developer:
a: chloroform-methanol-conc. ammonia (150:10:1)
b: benzene-acetone (3:1)

EXAMPLE 1

3-O-acetyl-4''-deoxydesmycosin

Acetic anhydride (56.0 μl, 5 equivalents) and 4-dimethylaminopyridine (3 mg, 0.2 equivalent) were added to 2', 4'-di-O-acetyl-4''-deoxydesmycosin (100 mg) dissolved in pyridine and the mixture was stirred at 55° C. for 3.5 hours.

TABLE 1

| | | | | MIC (μg/ml) | | | |
| | | | | compound | | | |
| test organisms | $R_3$ $R_2$ $R_1$ | OH —CHO —COCH$_3$ | OH —CHO —COCH$_2$CH$_3$ | OH —CHO —CO(CH$_2$)$_2$CH$_3$ | OH —CHO —COCH$_2$CH(CH$_3$)$_2$ | OH —CHO —COC$_6$H$_5$ | OH —CHO —COCH$_2$C$_6$H$_5$ |
|---|---|---|---|---|---|---|---|
| Staphylococcus aureus ATCC 6538P | | 0.4 | 0.4 | 0.4 | 0.4 | 0.2 | 0.1 |
| Staphylococcus aureus MS353 | | 0.2 | 0.2 | 0.4 | 0.4 | 0.2 | 0.2 |
| Staphylococcus aureus MS353 C36 | | 0.2 | 0.2 | 0.2 | 0.4 | 0.2 | 0.1 |
| Staphylococcus aureus MS353 A0* | | >100 | 12.5 | 25 | >100 | 50 | >100 |
| Staphylococcus aureus 0119* | | 100 | 25 | 25 | >100 | >100 | >100 |
| Staphylococcus aureus 0127* | | >100 | 12.5 | 25 | >100 | >100 | >100 |
| Staphylococcus epidermidis sp-al-1 | | 0.1 | ≦0.05 | ≦0.05 | 0.1 | 0.1 | ≦0.05 |
| Streptococcus pyogenes N.Y.5 | | ≦0.05 | ≦0.05 | ≦0.05 | ≦0.05 | ≦0.05 | 0.1 |
| Streptococcus pyogenes 1022* | | 50 | 12.5 | 12.5 | >100 | 25 | — |
| Streptococcus faecalis 1501 | | 0.8 | 0.4 | 0.2 | 0.4 | 1.6 | 0.4 |

TABLE 1-continued

| | | MIC (μg/ml) compound | | | | | |
|---|---|---|---|---|---|---|---|
| | $R_3$ | OH | OH | OH | OH | OH | OH |
| | $R_2$ | —CHO | —CHO | —CHO | —CHO | —CHO | —CHO |
| test organisms | $R_1$ | —COCH$_3$ | —COCH$_2$CH$_3$ | —CO(CH$_2$)$_2$CH$_3$ | —COCH$_2$CH(CH$_3$)$_2$ | —COC$_6$H$_5$ | —COCH$_2$C$_6$H$_5$ |
| Streptococcus agalaactiae 1020 | | 0.1 | 0.1 | 0.1 | ≦0.05 | 0.2 | 0.1 |
| Sarcina lutea ATCC 9341 | | ≦0.05 | ≦0.05 | ≦0.05 | ≦0.05 | ≦0.05 | ≦0.05 |
| Micrococcus flavus ATCC 10240 | | ≦0.05 | ≦0.05 | ≦0.05 | ≦0.05 | ≦0.05 | ≦0.05 |
| Corynebacterium diphtheriae P.Y.8 | | — | — | ≦0.05 | ≦0.05 | — | ≦0.05 |
| Bacillus subtilis ATCC 6633 | | 0.2 | 0.1 | 0.1 | 0.2 | 0.1 | 0.1 |
| Escherichia coli NIHJ-JC2 | | >100 | >100 | >100 | >100 | >100 | >100 |
| Escherichia coli B | | >100 | 100 | >100 | >100 | >100 | >100 |
| Klebsiella pneumoniae ATCC 10031 | | 25 | 25 | 25 | 25 | 25 | 25 |
| Salmonella typhosa H901 | | >100 | >100 | >100 | >100 | >100 | >100 |
| Salmonella enteritidis Gaertner | | >100 | >100 | >100 | >100 | >100 | >100 |
| Shigella flexineri type 3a | | 50 | 50 | 50 | 50 | 100 | 50 |
| Shigella sonnei E33 | | >100 | >100 | >100 | >100 | >100 | >100 |
| Proteus vulgaris OX19 | | 25 | 50 | 50 | 50 | 50 | 50 |
| Serratia marcescens | | >100 | >100 | >100 | >100 | >100 | >100 |
| Pseudomonas aeruginosa IAM 1095 | | >100 | 50 | >100 | >100 | >100 | >100 |

TABLE 2

| | | MIC (μg/ml) compound | | | | | |
|---|---|---|---|---|---|---|---|
| | $R_3$ | OH | OH | OH | OH | | |
| | $R_2$ | H | H | H | H | | |
| test organisms | $R_1$ | —COCH$_3$ | —COCH$_2$CH$_3$ | —COC$_6$H$_5$ | —COCH$_2$C$_6$H$_5$ | Erythromycin | Tylosin |
| Staphlococcus aureus ATCC 6538P | | 0.4 | 0.4 | 0.2 | 0.1 | 0.2 | 0.8 |
| Staphylococcus aureus MS353 | | 0.2 | 0.4 | 0.2 | 0.1 | 0.2 | 0.8 |
| Staphylococcus aureus MS353 C36 | | 0.2 | 0.2 | 0.1 | 0.1 | >100 | 0.4 |
| Staphylococcus aureus MS353 A0* | | >100 | >100 | >100 | >100 | >100 | >100 |
| Staphylococcus aureus 0119* | | >100 | >100 | >100 | >100 | >100 | >100 |
| Staphylococcus aureus 0127* | | >100 | >100 | >100 | >100 | >100 | >100 |
| Staphylococcus epidermidis sp-al-1 | | 0.1 | 0.1 | ≦0.05 | ≦0.05 | 0.2 | 0.4 |
| Streptococcus pyogenes N.Y.5 | | 0.1 | 0.1 | ≦0.05 | ≦0.05 | ≦0.05 | 0.1 |
| Streptococcus pyogenes 1022* | | >100 | >100 | >100 | — | >100 | >100 |
| Streptococcus faecalis 1501 | | 3.1 | 3.1 | 1.6 | 3.1 | 0.2 | 0.8 |
| Streptococcus agalacticae 1020 | | 0.8 | 0.4 | 0.2 | 0.4 | ≦0.05 | 0.2 |
| Sarcina lutea ATCC 9341 | | ≦0.05 | ≦0.05 | ≦0.05 | ≦0.05 | ≦0.05 | ≦0.05 |
| Micrococcus flavus ATCC 10240 | | ≦0.05 | ≦0.05 | ≦0.05 | ≦0.05 | 0.1 | ≦0.05 |
| Corynebacterium diphtheriae P.Y.8 | | — | — | — | ≦0.05 | ≦0.05 | ≦0.05 |
| Bacillus subtilis ATCC 6633 | | 0.1 | 0.1 | 0.2 | 0.2 | 0.1 | 0.2 |
| Escherichia coli NIHJ-JC2 | | >100 | >100 | >100 | >100 | 100 | >100 |
| Escherichia coli B | | >100 | 100 | >100 | >100 | >100 | >100 |
| Klebsiella pneumoniae ATTC 10031 | | 25 | 12.5 | 25 | 12.5 | 6.3 | 50 |
| Salmonella typhosa H901 | | >100 | >100 | >100 | >100 | 100 | >100 |
| Salmonella enteritidis Gaertner | | >100 | >100 | >100 | >100 | 100 | >100 |
| Shigella flexineri type 3a | | >100 | 100 | >100 | 25 | 12.5 | 50 |
| Shigella sonnei E33 | | >100 | >100 | >100 | >100 | 100 | >100 |
| Proteus vulgaris OX19 | | 100 | 100 | 100 | 100 | 50 | >100 |
| Serratia marcescens | | >100 | >100 | >100 | >100 | 100 | >100 |
| Pseudomonas aeruginosa IAM 1095 | | >100 | >100 | >100 | >100 | 100 | >100 |

The reaction mixture was poured into water, adjusted to pH 8–9 by adding aqueous ammonia and extracted twice with chloroform. After dehydrating the chloroform layer with anhydrous magnesium sulfate, the chloroform layer was concentrated in vacuo to obtain crude 3,2'-4'-tri-O-acetyl-4"-deoxydesmycosin. The product dissolved in a small amount of chloroform was charged on a column of silica gel (10 g, Merck, Art. 9385) and eluted with benzene-acetone (16:1–8:1). The fractions showing Rfb=0.4 were collected and concentrated in vacuo to obtain a purified product (44.0 mg). The product dissolved in methanol (5 ml) was heated at 55° C. for 16 hours to remove 2,4'-di-O-acetyl, and dried in vacuo to obtain 3-O-acetyl-4"-deoxydesmycosin (37.2 mg).

TLC: Rfa=0.32 (4"-deoxydesmycosin Rfa=0.32)

NMR (100 MHz, CDCl$_3$) δ ppm; 1.81 (s., 12—CH$_3$), 2.12 (s., —COCH$_3$), 2.50 (s., —N(CH$_3$)$_2$), 3.40 (s., 3"-OCH$_3$), 3.46 (s., 2"—OCH$_3$), 4.20 (d., H-1'), 4.63 (d., H-1"), 4.85 (t.d., H-15), 5.15 (d.d., H-3), 5.95 (d., H-13), 6.24 (d., H-10), 7.40 (d., H-11), 9.64 (s., CHO)

Mass (CI); 798 (MH+), 738 (MH+—CH$_3$COOH, 174.

EXAMPLE 2

3-O-propionyl-4"-deoxydesmycosin

In Example 1, acetic anhydride was replaced by propionic anhydride (76.3 μl) to obtain crude 3-O-propionyl-2',4'-di-O-Acetyl-4"-deoxydesmycosin. The product dissolved in small amount of chloroform was charged on a column of silica gel (10 g. Merck, Art. 9385) and eluted with benzene-acetone (12:1–8:1). The fractions showing Rfb=0.45 were collected and dried in vacuo to obtain a purified product (57.1 mg), which was de-2′,4′-di-O-acetylated by the same process as in Example 1 to obtain 3-O-propionyl-4″-deoxydesmycosin (47.5 mg, yield: 49.1%).

TLC: Rfa=0.34

NMR (100 MHz CDCl₃) δ ppm; 1.81 (s., 12—CH₃), 2.49 (s., N(CH₃)₂), 3.40 (s., 3″-OCH₃), 3.46 (s., 2″—OCH₃), 4.18 (d., H-1′), 4.63 (d., H-1″), 4.84 (t.d., H-15), 5.20 (d.d., H-3), 5.99 (d., H-13), 6.23 (d., H-10), 7.41 (d., H-11), 9.64 (s., CHO)

Mass (CI); 812 (MH+), 738 (MH+—CH₃CH₂COOH), 174

EXAMPLE 3

3-O-butyryl-4″-deoxydesmycosin

In Example 1, acetic anhydride was replaced by butyric anhydride (97.4 μl) to obtain crude 3-O-butyryl-2′,4′-di-O-acetyl-4″-deoxydesmycosin (98.6 mg).

The product was dissolved in small amount of chloroform and charged on a column of silica gel (10 g. Merck, Art. 9385) and eluted with benzene-acetone (16:1–8:1). The fractions showing Rfb=0.47 were collected and dried in vacuo to obtain a purified product (62.6 mg), which was dissolved in methanol (5 ml), heated at 55° C. for 6 hours, then concentrated in vacuo. Diluted ammonia was added to the residue and the mixture was extracted with chloroform. The extract was dried with anhydrous magnesium sulfate and dried in vacuo to obtain 3-O-butyryl-4″-deoxydesmycosin (51.7 mg, yield: 52.6%).

TLC; Rfa=0.35

NMR (100 MHz, CDCl₃) δ ppm; 1.81 (s., 3H, 12—CH₃), 2.49 (s., 6H, N (CH₃)₂), 3.40 (s., 3H, 3″—OCH₃), 3.46 (s., 3H, 2″—OCH₃), 4.18 (d., 1H, H-1′), 4.63 (d., 1H, H-1″), 4.87 (d.t., 1H, H-15) 5.20 (d.d., 1H, H-3), 5.98 (d., 1H, H-13), 6.23 (d., 1H, H-10), 7.40 (d., H, H-11), 9.66 (s., 1H, CHO)

Mass (CI); 826 (MH+), 808 (MH+-18), 738 (MH+—CH₃CH₂CH₂COOH), 563, 174

EXAMPLE 4

3-O-isovaleryl-4″-deoxydesmycosin

In Example 1, acetic anhydride was replaced by isovaleric anhydride (118 μl) and the reaction was continued for 5.5 hours to obtain crude 3-O-isovaleryl-2′,4′-di-O-acetyl-4″-deoxydesmycosin (98.1 mg).

The product dissolved in a small amount of chloroform was charged on a column of silica gel (10 g, Merck, Art. 9385) and eluted with benzene-acetone (16:1–10:1). The fractions showing Rfb=0.47 were collected and dried in vacuo to obtain a purified product (42.3 mg). The product was dissolved in methanol (5 ml) and the solution was heated at 55° C. for 16 hours. The reaction mixture was concentrated in vacuo, diluted aqueous ammonia was added to the residue and the mixture was extracted with chloroform. The extract was dried with anhydrous magnesium sulfate and concentrated in vacuo to obtain crude 3-O-isovaleryl-4″-deoxydesmycosin (32.8 mg). The product was charged on a column of silica gel (2 g, Merck, Art. 7747) and eluted with chloroform-methanol (50:1–10:1). The fractions showing Rfa=0.36 were collected and dried in vacuo to obtain the purified product (15.2 mg, yield: 15.2%).

TLC; Rfa=0.36

NMR (100 MHz, CDCl₃) δ ppm; 1.80 (s., 3H, 12—CH₃), 2.49 (s., 6H, N (CH₃)₂), 3.39 (s., 3H, 3″—OCH₃), 3.42 (s., 3H, 2″—OCH₃), 4.17 (d., 1H, H-1′), 4.62 (d., 1H, H-1″), 4.87 (d.t., 1H, H-15), 5.17 (d.d., 1H, H-3), 5.96 (d., 1H, H-13), 6.23 (d., 1H, H-10), 7.39 (d., 1H, H-11), 9.69 (s., 1H, CHO).

Mass (CI): 840 (MH+), 738 (MH+-isovaleric acid), 563, 174.

EXAMPLE 5

3-O-benzoyl-4″-deoxydesmycosin

Benzoic acid anhydride (134.7 mg, 5 equivalents) and 4-dimethylaminopyridine (14.5 mg, 1 equivalent) were added to 2′,4′-di-O-acetyl-4″-deoxydesmycosin (100 mg) dissolved in pyridine (1 ml) and the mixture was stirred at 55° C. for 21 hours. The reaction mixture was poured into water, the aqueous layer was adjusted with aqueous ammonia to pH 8–9, and the mixture was extracted twice with chloroform. The extract was dried with anhydrous magnesium sulfate and concentrated in vacuo. The residue was charged on a column of silica gel (10 g, Merck, Art. 9385) and eluted with benzene-acetone (20:1–8:1). The fractions showing Rfb=0.47 were collected and dried in vacuo to obtain 3-O-benzoyl-2′,4′-di-O-acetyl-4″-deoxydesmycosin (33.5 mg). The product was dissolved in methanol (5 ml), heated at 55° C. for 16 hours and concentrated in vacuo. The residue dissolved in chloroform was washed with diluted aqueous ammonia, dried with anhydrous magnesium sulfate and dried in vacuo to obtain 3-O-benzoyl-4″-deoxydesmycosin (27.7 mg, yield: 27.1%).

TLC; Rfa=0.33

NMR (100 MHz, CDCl₃) δ ppm; 1.83 (s., 12—CH₃), 2.43 (s., N(CH₃)₂, 3.39 (s., 3″—OCH₃), 3.42 (s., 2″—OCH₃), 4.10 (d., H-1′), 4.61 (d., H-1″), 4.91 (t.d., H-15), 5.48 (d.d., H-3), 6.02 (d., H-13), 6.25 (d., H-10), 7.30–7.60 (m., 4H, H-11, phenyl 3,4,5-proton), 7.95–8.16 (phenyl 2,6-proton), 9.66 (s., CHO).

Mass (CI): 738 (MH+—C₆H₅COOH), 174, 123.

EXAMPLE 6

3-O-phenylacetyl-4″-deoxydesmycosin

N,N′-dicyclohexylcarbodiimide (DCC) (49.1 mg, 2 equivalents) and phenylacetic acid (32.4 mg, 2 equivalents) and 4-dimethylaminopyridine (14.5 mg, 1 equivalent) were added to 2′,4′-di-O-acetyl-4″-deoxydesmycosin (100 mg) dissolved in dichloroethane (1 ml) and the mixture was stirred at 55° C. for 16 hours. The reaction mixture was filtered and the filtrate was washed with dichloroethane, then the filtrate and washing solution were combined and concentrated in vacuo to obtain crude 3-O-phenylacetyl-2′,4′-di-O-acetyl-4″-deoxydesmycosin. The product was purified by preparative silica gel thin layer chromatography (Merck, Art. 5717, 20×20 cm, one plate) using as a developer benzene-acetone (4:1). The spot showing Rf=0.35 was scratched and eluted with acetone. The eluate was dried in vacuo to obtain a purified product which was dissolved in methanol (5 ml), heated at 55° C. for 16 hours and concentrated in vacuo. The residue was extracted with chloroform, washed with aqueous ammonia, dried with anhydrous magnesium sulfate and concentrated in vacuo to obtain 3-O-phenylacetyl-4″-deoxydesmycosin (40 mg, yield: 44.7%).

TLC: Rfa=0.38

Mass (CI): 874 (MH+), 856 (MH+-18), 737 (MH+-137), 192, 174, 159, 137, 127.

EXAMPLE 7

3-O-acetyl-19-deformyl-4''-deoxydesmycosin

Acetic anhydride (58 μl, 5 equivalents) and 4-dimethylaminopyridine (3 mg, 0.2 equivalent) were added to 2',4'-di-O-acetyl-19-deformyl-4''-deoxydesmycosin (100 mg) dissolved in pyridine (1 ml) and the mixture was stirred at 50° C. for 3 hours. The reaction mixture was poured into dilute aqueous ammonia and extracted twice with chloroform. The chloroform layer was dried with anhydrous magnesium sulfate and concentrated in vacuo. Benzene-ethanol (1:1) was added to the residue for removing pyridine by azeotropic distillation and the mixture was concentrated in vacuo to obtain 3,2',4'-tri-O-acetyl-19-deformyl-4''-deoxydesmycosin, which was purified by preparative silica gel thin layer chromatography (Merck, Art. 5717, 20×20 cm, one plate) using as a developer benzene-acetone (4:1). The spot showing Rf=0.45 was scratched, extracted with acetone and dried in vacuo to obtain a purified product. The product was dissolved in methanol (10 ml) and heated at 55° C. for 16 hours, then dried in vacuo to obtain 3-O-acetyl-19-deformyl-4''-deoxydesmycosin (55 mg).

TLC: $Rfa=0.50$ (19-deformyl-4''-deoxydesmycosin $Rfa+0.46$)

NMR (100 MHz, CDCl$_3$) δ ppm; 1.80 (s., 3H, 12—CH$_3$), 2.05 (s., 3H, —COCH$_3$), 2.50 (s., 6H, —N(CH$_3$)$_2$), 3.39 (s., 3H, 3''—OCH$_3$), 3.46 (s., 3H, 2''—OCH$_3$), 4.18 (d., 1H, 1'-H), 4.62 (d., 1H, 1''-H), 4.90 (m., 1H, 15-H), 5.17 (d.d., 1H, 3-H), 5.93 (d., 1H, 13-H), 6.21 (d., 1H, 10-H), 7.31 (d., 1H, 11-H)

Mass (CI): 770 (MH+), 710 (MH+-60), 190, 174, 159, 127.

EXAMPLE 8

3-O-propionyl-19-deformyl-4''-deoxydesmycosin

In Example 7, acetic anhydride was replaced by propionic anhydride (76 μl) to obtain crude 3-O-propionyl-2',4'-di-O-acetyl-19-deformyl-4''-deoxydesmycosin, which was purified by preparative silica gel TLC as shown in Example 7. The purified product dissolved in methanol (10 ml), heated at 55° C. for 16 hours and dried in vacuo to obtain 3-O-propionyl-19-deformyl-4''-deoxydesmycosin (47 mg).

TLC: $Rfa=0.54$

NMR (100 MHz, CDCl$_3$) δ ppm; 1.79 (s., 3H, 12—CH$_3$) 2.50 (s., 6H, —N(CH$_3$)$_2$), 3.40 (s., 3H, 3''—OCH$_3$), 3.46 (s., 3H, 2''—OCH$_3$), 4.17 (d., 1H, 1'-H), 4.62 (d., 1H, 1''-H), 4.89 (m., 1H, 15-H), 5.19 (d.d., 1H, 3-H), 5.93 (d., 1H, 13-H), 6.21 (d., 1H, 10-H), 7.31 (d., 1H, 11-H)

Mass (CI): 784 (MH+), 710 (MH+-74), 190, 174, 159, 127.

EXAMPLE 9

3-O-benzoyl-19-deformyl-4''-deoxydesmycosin

Benzoic acid anhydride (209 mg, 5 equivalents) and 4-dimethylaminopyridine (22.6 mg, 2 equivalents) were added to 2',4'-di-O-acetyl-19-deformyl-4''-deoxydesmycosin (150 mg) dissolved in pyridine (1.5 ml), and the mixture was stirred at 55° C. for 21 hours. The reaction mixture was poured into water; the aqueous layer was adjusted to pH 9 by adding aqueous ammonia, and the mixture was extracted twice with chloroform. The extract was dried with anhydrous magnesium sulfate and concentrated in vacuo. The residue was charged on a column of silica gel (Merck, Art. 9385, 10 g) and eluted with benzen-acetone (20:1-12:1). The fractions showing Rfb=0.6 were collected and dried in vacuo to obtain 3-O-benzoyl-2',4'-di-O-acetyl-19-deformyl-4''-deoxydesmycosin (86.6 mg). The product was dissolved in methanol (5 ml) and heated at 55° C. for 16 hours, then concentrated in vacuo. The residue dissolved in chloroform was washed with 7% aqueous ammonia, dried with anhydrous magnesium sulfate and dried in vacuo to obtain 3-O-benzoyl-19-deformyl-4''-deoxydesmycosin (69.2 mg, yield: 45.0%).

TLC; $Rfa=0.57$

NMR (100 MHz, CDCl$_3$) δ ppm; 1.82 (s., 12—CH$_3$), 2.44 (s., N(CH$_3$)$_2$), 3.39 (s., 3''—OCH$_3$), 3.43 (s., 2''—OCH$_3$), 4.12 (d., H-1'), 4.61 (d., H-1''), 4.91 (t.d., H-15), 5.53 (d.d., H-3), 5.98 (d., H-13), 6.24 (d., H-10), 7.36~7.57 (m., 4H, H-11, phenyl 3,4,5-proton), 7.90~8.12 (m., phenyl 2,6-proton)

Mass (CI): 832 (MH+), 710 (MH+-C$_6$H$_5$COOH), 174, 123.

EXAMPLE 10

3-O-phenylacetyl-19-deformyl-4''-deoxydesmycosin

In Example 6, 2',4'-di-O-acetyl-4''-deoxydesmycosin was replaced by 2',4'-di-O-acetyl-19-deformyl-4''-deoxydesmycosin to obtain crude 3-O-phenylacetyl-2',4'-di-O-acetyl-19-deformyl-4''-deoxydesmycosin, which was purified by preparative silica gel TLC (Merck, Art. 5717, 20×20 cm, one plate) developed with benzene-acetone (3:1). The spot showing Rf=0.6 was scratched and eluted with acetone. The eluate was dried in vacuo to obtain the purified product, which was deacetylated according to the method in Example 6 to obtain 3-O-phenylacetyl-19-deformyl-4''-deoxydesmycosin (20 mg, yield: 19.2%).

TLC; $Rfa=0.58$

NMR (100 MHz, CDCl$_3$) δ ppm; 1.78 (s., 12—CH$_3$), 2 51 (s., N(CH$_3$)$_2$, 3.40 (s., 3''—OCH$_3$), 3.46 (s., 2''-OCH$_3$), 3.61 (s., —CH$_3$)$_2$, 3.90 (d., H-1'), 4.62 (d., H-1''), 4.89 (m., H-15), 5.17 (d.d., H-3), 5.91 (d., H-13), 6.20 (d., H-10), 7.27 (s., phenyl proton), 7.31 (d., H-11)

Mass (CI): 846 (MH+), 709, 192, 174, 159, 137, 127.

What is claimed is:

1. A compound of the formula wherein R$_1$ is lower alkyl, phenyl lower alkyl or substituted phenyl-lower alkyl, R$_2$ is hydrogen or —CHO and R$_3$ is hydrogen or hydroxyl, or a non-toxic salt thereof.

2. A compound according to claim 1, wherein R$_3$ is hydroxyl.

3. A compound according to claim 1, which is

3-O-acetyl-4''-deoxydesmycosin,
3-O-propionyl-4''-deoxydesmycosin,
3-O-butyryl-4''-deoxydesmycosin,
3-O-isovaleryl-4''-deoxydesmycosin,
3-O-benzoyl-4''-deoxydesmycosin,
3-O-phenylacetyl-4''-deoxydesmycosin,
3-O-acetyl-19-deformyl-4''-deoxydesmycosin,
3-O-propionyl-19-deformyl-4''-deoxydesmycosin,
3-O-benzoyl-19-deformyl-4''-deoxydesmycosin or
3-O-phenylacetyl-19-deformyl-4''-deoxydesmycosin.

* * * * *